(12) United States Patent
Kalpin et al.

(10) Patent No.: US 8,512,286 B2
(45) Date of Patent: Aug. 20, 2013

(54) DETECTING A FULL RESERVOIR OF AN IMPLANTABLE INFUSION DEVICE

(75) Inventors: Scott L. Kalpin, Minneapolis, MN (US); James M. Haase, Maplewood, MN (US)

(73) Assignee: Medtronic, Inc., Minneapolis, MN (US)

( * ) Notice: Subject to any disclaimer, the term of this patent is extended or adjusted under 35 U.S.C. 154(b) by 140 days.

(21) Appl. No.: 13/088,619

(22) Filed: Apr. 18, 2011

(65) Prior Publication Data
US 2012/0265141 A1 Oct. 18, 2012

(51) Int. Cl.
*A61M 37/00* (2006.01)

(52) U.S. Cl.
USPC .............. 604/132; 604/890.1; 604/891.1; 604/67; 604/131

(58) Field of Classification Search
USPC .............. 604/890.1, 891.1, 892.2, 65, 67, 604/131–133, 150
See application file for complete search history.

(56) References Cited

U.S. PATENT DOCUMENTS

| 4,443,218 A * | 4/1984 | DeCant et al. .............. 604/67 |
| 4,573,994 A * | 3/1986 | Fischell et al. ............ 604/891.1 |
| 5,090,963 A * | 2/1992 | Gross et al. ............... 604/132 |
| 5,507,737 A * | 4/1996 | Palmskog ................ 604/891.1 |
| 5,707,361 A * | 1/1998 | Slettenmark ............ 604/131 |
| 6,152,898 A * | 11/2000 | Olsen ........................ 604/93.01 |
| 6,635,049 B1 | 10/2003 | Robinson |
| 2010/0125246 A1 * | 5/2010 | Kalpin ...................... 604/151 |

FOREIGN PATENT DOCUMENTS

WO WO 2007/127828 11/2007

* cited by examiner

*Primary Examiner* — Quynh-Nhu H Vu
(74) *Attorney, Agent, or Firm* — Mueting Raasch & Gebhardt PA

(57) ABSTRACT

An implantable infusion device includes a housing and a collapsible member and an interference member disposed within the housing. The collapsible member defines a reservoir for containing fluid and has an outer surface that moves between an empty position and a full position in response to a change in volume of fluid contained in the reservoir. The interference member is configured to engage the outer surface of the collapsible member as the reservoir approaches the full position and to cause pressure in the reservoir to increase following engagement with the surface of the collapsible member and concomitant fluid introduction into the reservoir. The infusion device further includes a pressure sensor in communication with the reservoir, which can be used to determine whether the reservoir is full by measuring characteristic pressures associated with the interference member engaging the outer surface of the collapsible member and concomitant fluid introduction into the reservoir.

21 Claims, 11 Drawing Sheets

DETECTING A FULL RESERVOIR OF AN IMPLANTABLE INFUSION DEVICE

FIELD

The present disclosure relates generally to implantable medical devices, and more particularly to systems and methods for detecting whether a reservoir of a refillable implantable infusion device is full.

BACKGROUND

Implantable infusions systems have been used to treat a variety of diseases, such as spasticity, pain and cancer by targeting drug delivery to a selected area of a patient. Therapies employing such systems have proven to be very helpful for patients for which systemic therapy is not effective, possible, or practicable. The implantable systems include an implantable infusion device containing a reservoir for housing the drug and a catheter coupled to the reservoir to direct the drug to the target area. The devices typically include a pump or mechanism for driving fluid from the reservoir, or withdrawing fluid from the reservoir, and through the catheter.

Many implantable infusion devices are configured to allow the reservoir to be transcutaneously refilled. Clinicians who refill the reservoirs of implantable infusion devices would benefit from an indication of reservoir "fullness" during the refill procedure. Such an indication may also increase conformance by ensuring that the reservoir repeatedly reaches a completely full status each time the reservoir is refilled.

Some implantable infusion devices have an over-pressurization mechanism (OPM) that prevents overfilling of the reservoir. The OPM may serve as a valve that closes an entry port into the reservoir when the reservoir is full. Closing the OPM valve results in increased pressure upstream of the valve, which can be felt by a clinician injecting fluid into the reservoir as increased resistance to syringe plunger advancement. This tactile feedback can be used by experienced clinicians as feedback that the reservoir has been filled.

However, due to manufacturing tolerances, the OPM valve is typically set to close when the reservoir is slightly beyond the desired fill level. As such, the OPM valve may not close every time that a reservoir is refilled. One way to ensure that the OPM valve closes is to reduce the reservoir volume at which the OPM valve closes or to increase the volume of drug in the syringe used to refill the reservoir. Either of these two scenarios would frequently result in undesirable waste of drug.

SUMMARY

This disclosure, among other things, describes devices, systems and methods for detecting when a reservoir of an implantable infusion device reaches fullness during a filling procedure. Infusion devices described herein are configured to create a detectable pressure increase in the reservoir when the reservoir becomes full during a refill procedure. A pressure sensor in communication with the reservoir, and electronics operably coupled to the pressure sensor, may be used to measure pressure in the reservoir and to determine whether a pressure increase characteristic of the reservoir being full is detected. If such as characteristic pressure increase is observed, a clinician refilling the reservoir may be alerted to stop filling the reservoir.

In various embodiments described herein, an implantable infusion device includes a housing and a collapsible member and an interference member disposed in the housing. The collapsible defines a reservoir for containing a variable volume of fluid therein and has an outer surface that moves between an empty position and a full position in response to a change in volume of fluid contained in the reservoir. The interference member is configured to engage the outer surface of the collapsible member as the reservoir approaches the full position and to cause pressure in the reservoir to increase following engagement with the surface of the collapsible member and concomitant fluid introduction into the reservoir. The infusion device also includes a pressure sensor in communication with the reservoir and includes electronics operably coupled to the pressure sensor for detecting the increase in pressure associated with engagement of the interference member with the surface of the collapsible member and concomitant fluid introduction into the reservoir. The electronics may be configured to determine whether a sensed pressure increase is indicative of engagement of the interference member with the outer surface of the collapsible member and concomitant fluid introduction into the reservoir, which is indicative of the reservoir being full. Data regarding the sensed pressure or whether the reservoir is full may be sent to an external device via telemetry for display to provide feedback regarding the full status of the reservoir during a refill procedure. Accordingly, a user may cease infusion of fluid into the reservoir once the display indicates that the reservoir is full.

Systems and method employing such infusion devices are also discussed herein.

One or more embodiments of the systems, devices and methods described herein may provide one or more advantages over prior systems, devices and methods for detecting when a reservoir of an implantable infusion device reaches fullness during a filling procedure. For example, the devices, methods and systems employed herein may allow for a display that the reservoir is full, as opposed to tactile feedback associated with OPMs, so that clinicians may more reproducibly stop filling a reservoir when the reservoir is full. This will increase reproducibility of therapy and perhaps result in more effective therapy across populations by reducing variability in full status. Of course, the devices methods and systems described herein may also employ OPMs, which can provide an additional safety feature in case of an error in the reservoir full detection system. These and other advantages of one or more embodiments of the methods and systems described herein will be apparent to those of skilled in the art upon reading the following detailed description.

BRIEF DESCRIPTION OF THE DRAWINGS

The accompanying drawings, which are incorporated into and form a part of the specification, illustrate several embodiments of the present disclosure and, together with the description, serve to explain the principles of the disclosure. The drawings are only for the purpose of illustrating embodiments of the disclosure and are not to be construed as limiting the disclosure.

Figure 1:
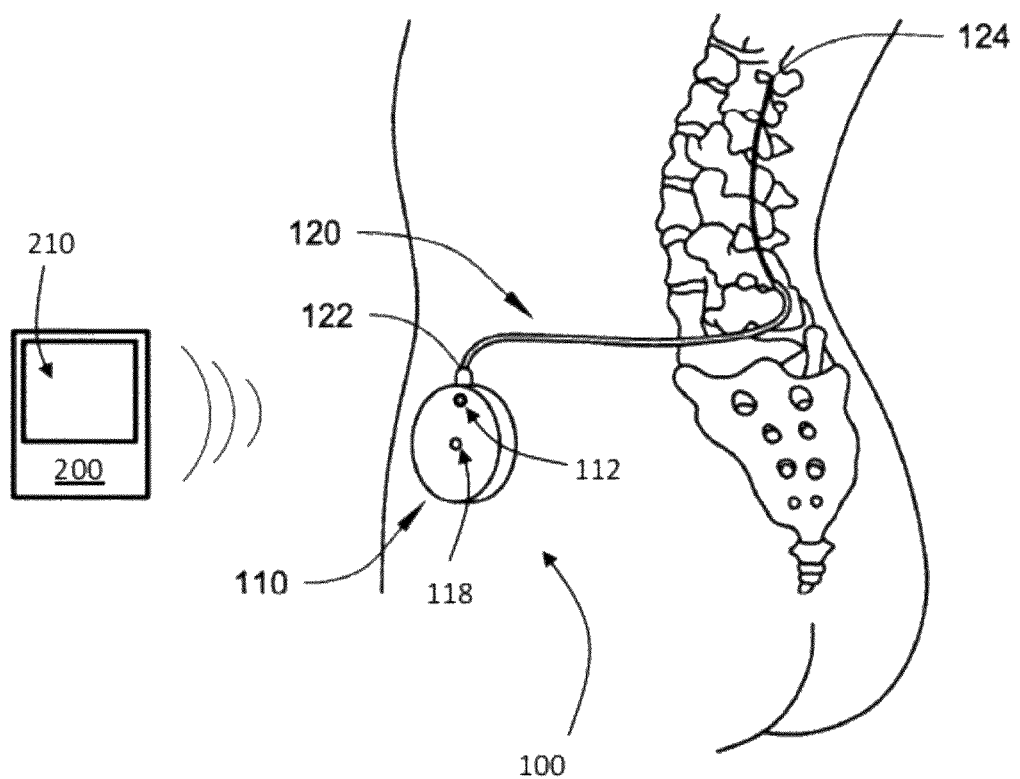
FIG. 1 is schematic view showing an infusion system implanted in a patient, along with an external device.

The schematic drawings presented herein are not necessarily to scale. Like numbers used in the figures refer to like components, steps and the like. However, it will be understood that the use of a number to refer to a component in a given figure is not intended to limit the component in another figure labeled with the same number. In addition, the use of different numbers to refer to components is not intended to indicate that the different numbered components cannot be the same or similar.

DETAILED DESCRIPTION

In the following detailed description, reference is made to the accompanying drawings that form a part hereof, and in which are shown by way of illustration several embodiments of devices, systems and methods. It is to be understood that other embodiments are contemplated and may be made without departing from the scope or spirit of the present disclosure. The following detailed description, therefore, is not to be taken in a limiting sense.

All scientific and technical terms used herein have meanings commonly used in the art unless otherwise specified. The definitions provided herein are to facilitate understanding of certain terms used frequently herein and are not meant to limit the scope of the present disclosure.

As used in this specification and the appended claims, the singular forms "a", "an", and "the" encompass embodiments having plural referents, unless the content clearly dictates otherwise.

As used in this specification and the appended claims, the term "or" is generally employed in its sense including "and/or" unless the content clearly dictates otherwise.

As used herein, "have", "having", "include", "including", "comprise", "comprising" or the like are used in their open ended sense, and generally mean "including, but not limited to."

As used herein, "full" or the like, as it relates to a reservoir volume means a volume to which the reservoir is intended to be filled, and does not necessarily, and often does not, refer to the maximum volume of fluid that the reservoir is capable of containing. For example, a 20 ml reservoir in an implantable infusion device may be capable of containing 22 ml or more of fluid. However, for the purposes of device and therapy reliability, it is often desired or intended for the reservoir to be refilled to a volume of 20 ml. Thus, the intended volume of 20 ml of such a device would be the full volume for the purposes of this disclosure. Regardless of the intended volume of the reservoir, it will be understood that "full" may include +/−5% of the intended full volume, as manufacturing variability and other design and use constraints often make it difficult or impracticable to precisely make each device perform identically with regard to reservoir full status. Full may refer to the point at which a surface of a collapsible member defining the reservoir contacts an interference member, as described herein Any direction referred to herein, such as "top", "bottom", "left", "right", "upper", "lower", and other directions or orientations are described herein for clarity in reference to the figures and are not intended to be limiting of an actual device or system. Devices and systems described herein may be used in a number of directions and orientations.

As used herein, "concomitant," as it relates to introduction of fluid into a reservoir in relation to engagement of a surface of a collapsible member defining the reservoir with an interference member, means the fluid is introduced at the time the surface of the collapsible member initially engages the interference member and continues following the initial engagement.

This disclosure relates to, among other things, devices, systems and methods for detecting when a reservoir of an implantable infusion device reaches fullness during a filling procedure. Infusion devices described herein are configured to create a detectable pressure increase in the reservoir when the reservoir becomes full during a refill procedure. A pressure sensor in communication with the reservoir, and electronics operably coupled to the pressure sensor, may be used to measure pressure in the reservoir and to determine whether a pressure increase characteristic of the reservoir being full is detected. If such as characteristic pressure increase is observed, a clinician refilling the reservoir may be alerted or notified and may stop filling the reservoir.

The devices, systems and methods described herein may be employed with any suitable implantable infusion system. FIG. 1 shows an example of an infusion system 100 that may be employed in accordance with the teachings presented herein. The infusion system depicted in FIG. 1 includes an infusion device 110 and a catheter 120. The catheter 120 is operably coupled to the infusion device 110 such that the catheter 120 is in fluid communication with a reservoir (not shown in FIG. 1) of the device 110. The depicted infusion device 110 includes a refill port 118 in communication with the reservoir, which is disposed within the housing of the device 110. The supply of therapeutic agent in the reservoir may be replenished via the refill port 118. The infusion device 110 may include any suitable mechanism or structure capable of delivering one or more fluids to a patient. The structures used to drive fluids in the infusion devices may be powered (e.g., piston pumps, diaphragm pumps, peristaltic pumps, etc.), may be activated based on pressure to drive fluid out of a reservoir (e.g., using collapsing diaphragms, expanding bladders, osmotic, etc.), or the like. The infusion device 110 may contain a catheter access port 112 in communication with the catheter 120 at a location upstream of the reservoir.

The infusion system 100 depicted in FIG. 1 is shown implanted in a patient. The proximal end 122 of the catheter 120 is coupled to the infusion device 110. The infusion device 110 may be surgically implanted in any suitable location, such as subcutaneously in the pectoral, abdominal or other region of the subject's body. The distal end 124 of the catheter 120 is implanted in a patient such that the distal end 124 is located at the selected internal delivery site in the patient (in the intrathecal space of the patient as depicted in FIG. 1, the cerebroventricles, or elsewhere as desired).

An external device 200 capable of wireless communication with the implanted infusion device 110 is also shown in FIG. 1. The depicted external device 200 includes a display 210 for presenting information to a user, such as a healthcare provider. In various embodiments, the external device 210 is capable of presenting information to the user that the reservoir has reached fullness.

Any suitable external device, such as a programmer (e.g., a Medtronic, Inc. N'Vision® clinician programmer or a Medtronic, Inc. myPTM® patient programmer), a tablet computer, a smart phone, a personal data assistance, a laptop computer, or the like, may be employed, provided that it is capable of communicating with the implanted infusion device. In some embodiments, the external device 200 is a desktop computer with an associated monitor serving as the display 210.

Referring now to FIGS. 2-13, schematic cross-sectional drawings of various embodiments of implantable infusion devices configured to allow detection of when a reservoir is full are shown. Only selected components of the infusion device are shown for purposes of clarity. The depicted infusion devices include a refill port 118 in communication with reservoir 48 for containing a variable volume of fluid. A septum 42 seals a port chamber 44 relative to an exterior of the device housing 130.

The reservoir 48 is defined by a collapsible member 50, which in the depicted embodiments is a bellows-type reservoir having an accordion-like collapsible, generally cylindrical wall 52. However, it will be understood that any type of collapsible reservoir, such as an expandable and collapsible bag, an elastomeric balloon-type reservoir, or the like, may be employed.

In the depicted embodiment, the collapsible member 50 is disposed in a chamber 65 defined in part by a bulkhead 60 that partitions the housing 130. The bulkhead 60 serves to isolate the reservoir 48 from other selected components of the device 110, such as certain control electronics. Of course, the chamber 65 may be defined by a structure contained within and fully separate from the housing 130. At least a portion of the collapsible member 50 (collapsible wall 52 in the depicted embodiment), is connected and sealed to a surface of the bulkhead 60. Of course, it will be understood that with reservoirs other than bellows-type reservoirs, it may not be desirable to attach a portion of the collapsible member 50 to the surface 62 of the bulkhead 60, and in some cases a bulkhead 60 may not be desired.

Regardless of the type of collapsible member 50 employed and whether a bulkhead 60 is employed, the collapsible member 50 has a surface 56 that moves between an empty position (see, e.g., FIGS. 2, 5, and 10) and a full position (see, e.g., FIGS. 3, 4, 6, 7, 8 and 11) in response to a changes in volume of fluid contained in the reservoir 48. As the reservoir 48 approaches the full position, surface 56 engages with an interference member, which may be an interior surface 64 of the housing 130 that defines a portion of the chamber 65 (see, e.g., FIGS. 2-9), a spring member 400 (see, e.g., FIGS. 10-12), which may be attached to the interior surface 64 of the housing 130, or the like. The interference member is positioned such that it contacts the surface 56 at the reservoir full position (e.g., within +/−5% of the intended full volume). Further infusion of fluid through refill port 118 causes an increase in pressure within the reservoir 48 due to interaction between surface 56 and interference member, which is detected by pressure sensor 14. However, in any case, the collapsible member 50 and the interference member are configured so that at least some further expansion of the reservoir 48 may occur after the surface 56 engages the interference member.

The pressure sensor 14 may be located anywhere such that it can detect the increase in pressure associated with engagement of the interference member with the surface 56 with concomitant fluid introduction into the reservoir 48. In the depicted embodiment, the pressure sensor is located in chamber 44 defined by the refill port 118.

Figure 2:
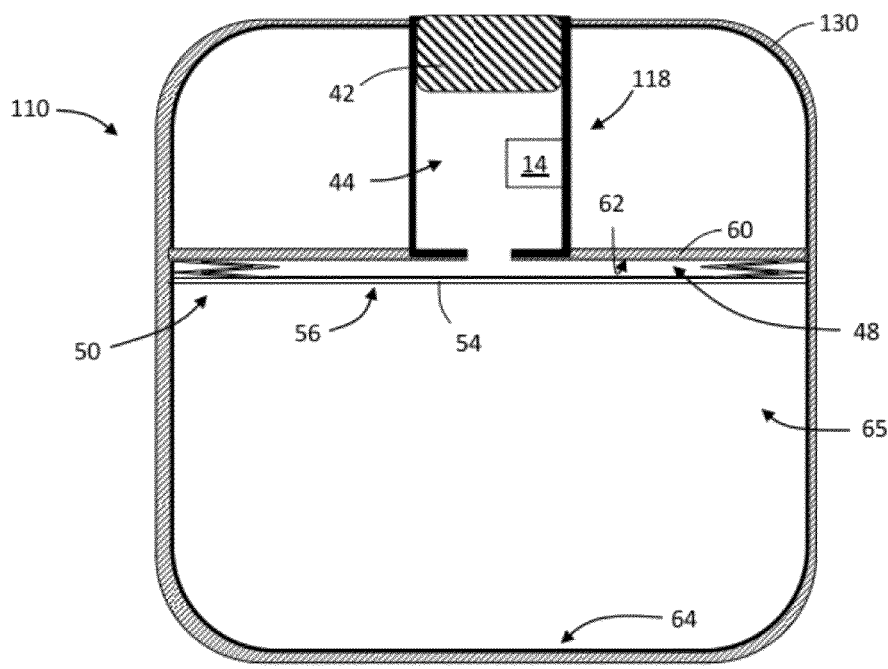
FIGS. 2-13 are schematic cross-sectional views showing selected components of implantable infusion devices in accordance with various embodiments described herein.
Figure 3:
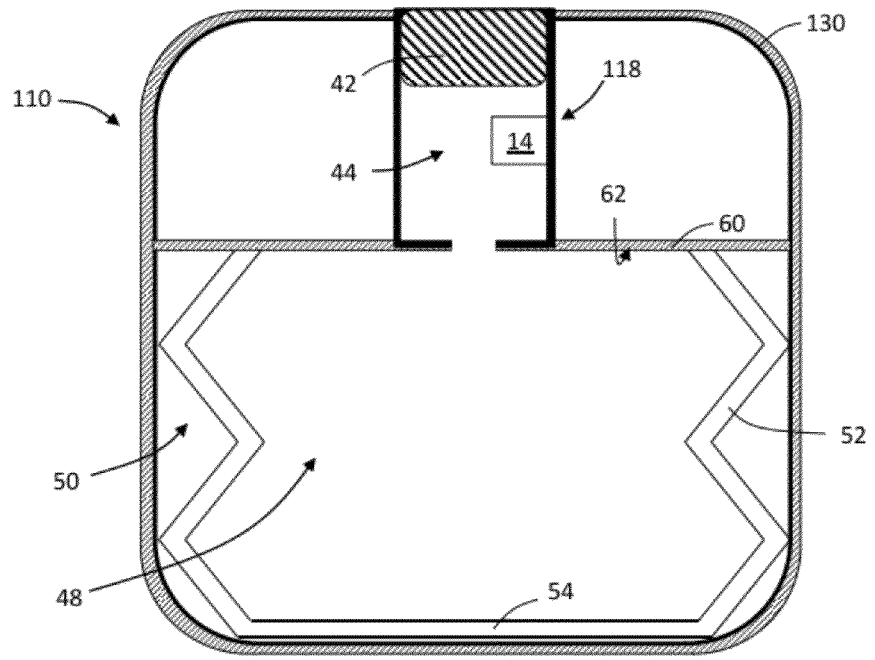

Referring now specifically to FIGS. 2-3, the interference member that engages the surface 56 of the collapsible member 50 is the bottom interior surface 64 of the housing 130. A propellant is disposed in chamber 65, which surrounds the reservoir 48 and biases the surface 56 of the collapsible member 50 to the empty position (see FIG. 2). As fluid is introduced into the reservoir 48 via refill port 118, the surface 56 moves towards the full position (see FIG. 3). Pressure in the reservoir 48 increases due to a decrease in volume occupied by the propellant in the chamber 65. The inventors have found that the collapsible member 50, bulkhead 60, propellant chamber 65, and propellant can be configured such that at a constant rate of infusion of fluid into the reservoir, the rate of change of pressure ($\delta P/\delta T$) over the majority of the volume of the reservoir 48 remains nearly constant. However, when the surface 56 of the collapsible member 50 engages the bottom interior surface 64 of the housing 130 while additional fluid is being added, a rapid rise in pressure is observed and the rate of change of pressure ($\delta P/\delta T$) increases. This increase in pressure or increase in rate of pressure increase can be detected by the pressure sensor 14.

In the embodiment depicted in FIGS. 2-3, the bottom interior surface 64 of the housing 130 is configured to contact and engage nearly the entire surface 56 of the collapsible member 50 at the same time, or within a very short period of time, as the reservoir 48 is being filled.

Figure 4:
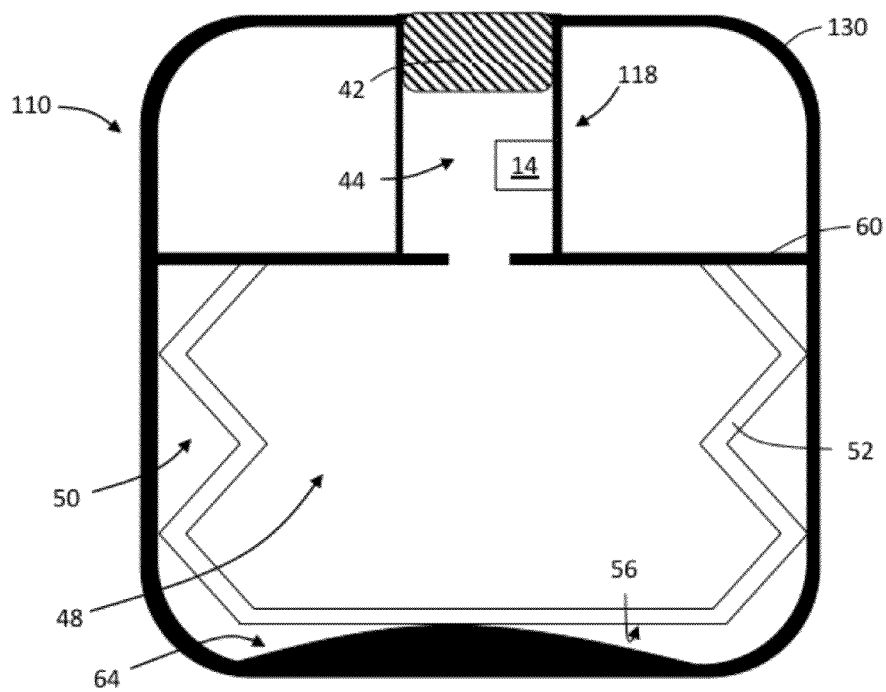

As shown in FIG. 4, the bottom interior surface 64 of the housing 130 may be shaped such that only a portion of the surface initially contacts the surface 56 of the collapsible member 50 as the reservoir 48 is filled. This initial contact reflects the full volume of the reservoir 48. Further infusion of fluid into the reservoir will cause more of the surface 56 of the collapsible member 50 to engage the bottom interior surface 64 of the housing 130, which in the depicted embodiment is convex. As additional fluid is introduced into the reservoir 48 and more surface contact between surface 56 and surface 64 is made, greater pressure increases and rates of pressure increases are observed in reservoir 48 and detectable by pressure sensor 14.

While the shape of the bottom interior surface 64 of the housing 130 is depicted in FIG. 4 as being convex, it will be understood that the surface 64 may be shaped in any suitable manner such that a portion (e.g., less than 50%, less than 40%, less that 30%, less than 20%, less than 10%, or less than 5%) of the surface 64 is configured to engage the surface 56 of the collapsible member 50 when the reservoir 48 is full, with additional surface contact occurring upon additional fluid being added to the reservoir.

Figure 5:
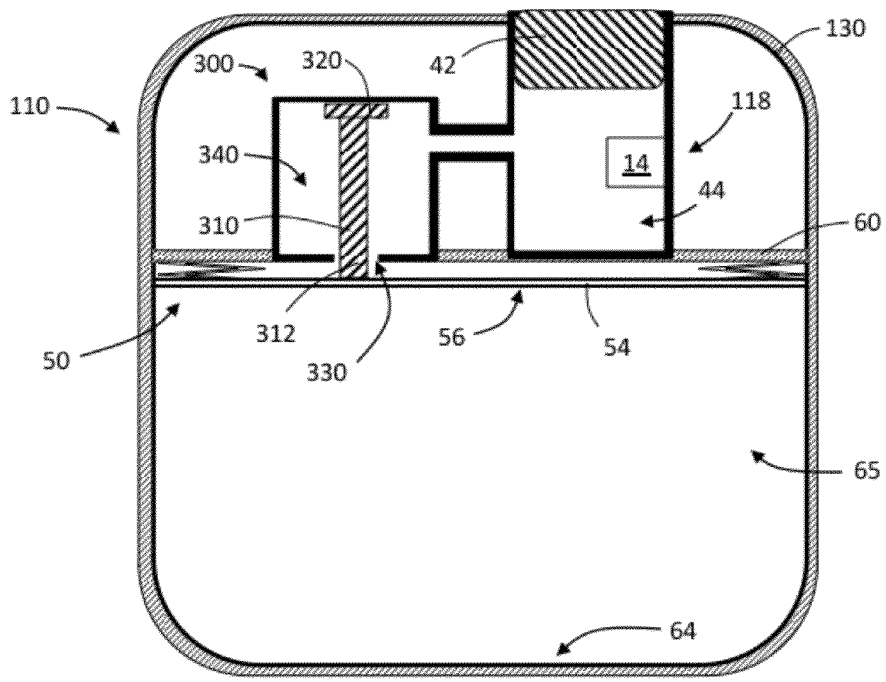
Figure 6:
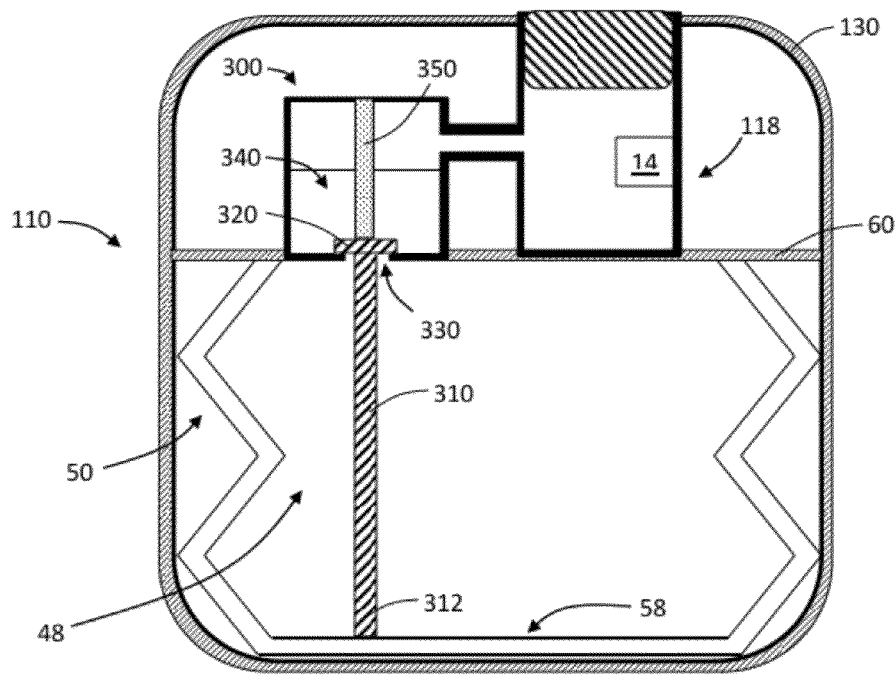

Referring now to FIGS. 5-6, embodiments of infusion devices 110 having an over-pressurization mechanism (OPM) 300 are shown. The OPM 300 is positioned within a transfer chamber 340 that forms a portion of the refill passageway and is, therefore, fluidly coupled to both the refill port 118 and the reservoir 48. Any suitable OPM 300 may be employed, such as those described in, for example, WO 2007/127828 and U.S. Pat. No. 6,152,898, which patent and published patent application are hereby incorporated herein by reference in their respective entireties to the extent that they do not conflict with the present disclosure.

In the embodiment depicted in FIGS. 5-6, the OPM 300 includes a valve assembly having a telescoping cylindrical valve body 310 slidable within a valve passageway 330 formed in the bulkhead 60. A clearance exists between a diameter of the valve body 310 and the valve passageway 330 so that fluid may flow between the transfer chamber 340 and the reservoir 48 during a refill process. A cylindrical or flanged portion or head 320 may be formed at a first, upper end of the valve body 310. The head 320 has an outer diameter larger than the diameter of the valve body 310 and valve passageway 330. A sealing member (not shown) such as an O-ring, may be located on the valve body 310 proximate the head 320. The sealing member may permit selective sealing of the valve passageway 330.

The OPM 300 may further include a biasing member (not shown), such as a coil spring, positioned to contact the valve body 310 and bias a free distal end 312 of the valve body 310 to abut a reservoir surface 58 that is generally opposed to (i.e., on the opposite side of) the surface 56 of the collapsible member 50 that contacts the interference member, e.g., the bottom interior surface 64 of the housing 130. The biasing member may bias the free distal end 312 of the valve body 310 to abut the reservoir surface 58 as it moves from the empty position (FIG. 5) to the full position (FIG. 6). The OPM may include a guide member 350 that serves to ensure proper axial movement of the valve body 310 and to constrain biasing member, e.g. spring (not shown), against lateral movement over all, or substantially all, of the valve plunger's travel.

As depicted in FIG. 6, when the reservoir is full, the valve body 310 extends to an extent that head (or sealing member—not shown) sealing engages the valve passageway 330 and prevents further infusion of fluid into the reservoir 48. However, it is often preferred that the OPM 300 is configured such that the valve passageway 330 closes or is sealed at a volume slightly beyond full (e.g., 1%-10% of reservoir full volume). For example, if the reservoir full volume is 20 ml, it may be desirable for the OPM valve to close at a reservoir volume of between about 20.2 ml to 22 ml, to minimize wasted drug. That is, if a refill syringe is loaded with 20.0 ml of a fluid drug composition and if the OPM were configured to close the OPM valve at a reservoir volume of less than 20 ml, drug would remain in the syringe and would be wasted.

Thus, it may be desirable to allow an additional small amount of fluid (e.g., 1% to 10% of reservoir full volume) to be introduced into a "full" reservoir to avoid wasting of drug. Such small additional amounts of fluid can be well tolerated by most infusion devices.

However, manufacturing tolerances for infusion devices as depicted in FIGS. 5-6 would be very tight. That is, there is very little room of additional fluid in the reservoir beyond full, and the OPM 300 would need to be set to close at, or very close to, reservoir full volume. For example and with reference to FIG. 6, the bottom interior surface 64 of the housing 130 is configured to contact and engage nearly the entire surface 56 of the collapsible member 50 at the same time, or within a very short period of time, of the reservoir 48 becoming full, and thus limits further expansion of the reservoir 48. Thus, the OPM 300 valve should be configured to close or seal at or before the reservoir full volume in the depicted embodiment. However, as additional fluid infusion into the reservoir 48 is somewhat constrained by the volume of the chamber 65, an OPM may not be needed in such an embodiment.

Figure 7:
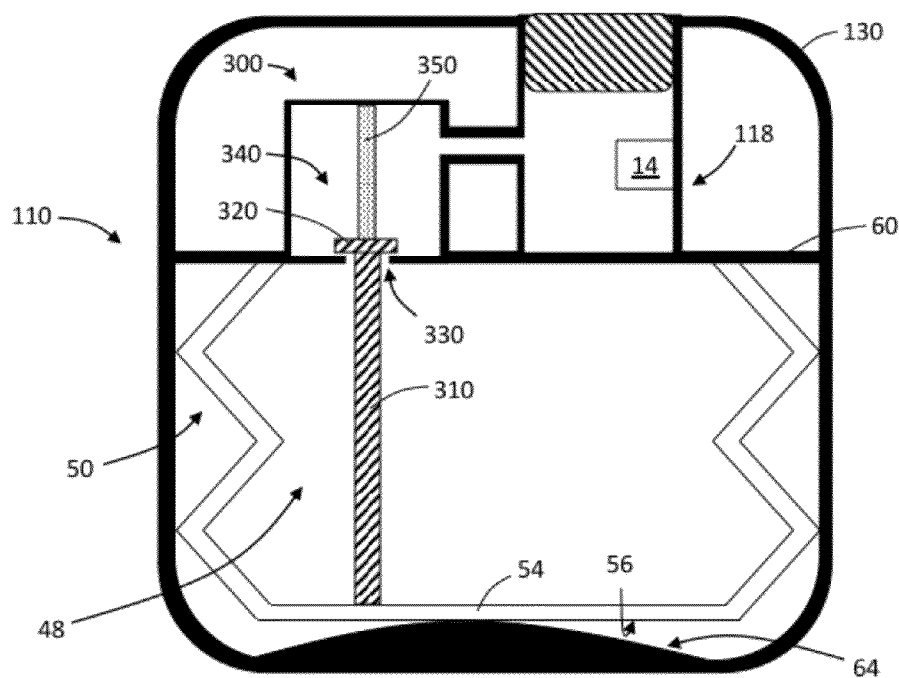

One way to overcome the issue associated with tight manufacturing tolerances described above with regard to the embodiment depicted in FIGS. 5-6 is addressed in the embodiment depicted in FIG. 7, where the bottom interior surface 64 of the housing 130 is shaped such that a portion (e.g., less than 50%, less than 40%, less that 30%, less than 20%, less than 10%, or less than 5%) of the surface 64 is configured to engage the surface 56 of the collapsible member 50 when the reservoir 48 is full, with additional surface contact occurring with additional fluid being added to the reservoir 48. In FIG. 7, the reservoir 48 is depicted as full, and introduction of additional fluid into the reservoir 48 will cause an increase in pressure detectable by pressure sensor 14, which can be determined by electronics of the device 110 to be indicative of a full reservoir. An alert, alarm or notification may be presented to a user to indicate full status.

Additionally, further introduction of fluid into the reservoir 48 will cause further movement of portions of the surface 56 of the collapsible member 50 towards the surface 64 of the housing 60, allowing further extension of the OPM valve body 310 and sealing of the valve passageway 330. Upon closing or sealing of the OPM valve passageway 330, an increase in pressure is observed upstream of the valve with continued attempted infusion of fluid into the refill port 118. This increase in pressure can be detected by experienced clinicians as feedback that the reservoir is full. Thus, a device 110 configured as depicted in FIG. 7 may allow for both an indication of reservoir full status via pressure sensor 14 and operably coupled electronics and tactile feedback associated with OPM 300 valve closure, which can provide an additional safety feature in cases of error in the reservoir full status detection components.

In many cases, however, to work effectively, the wall 54 forming the surface 56 of the collapsible member 50 would desirably be sufficiently flexible and resilient to allow for further advancement of the surface 56 beyond the reservoir full position to conform to the shape of the surface 64 of the housing 60. Preferably the surface 56 would also return substantially to its initial conformation as the reservoir 48 empties so that upon reservoir filling, the surface 56 can again contact only a portion of the surface 64 of the housing 130 (in this case the apex of the convex portion) when the reservoir is full, allowing detection of a pressure response indicative of reservoir full status.

Figure 8:
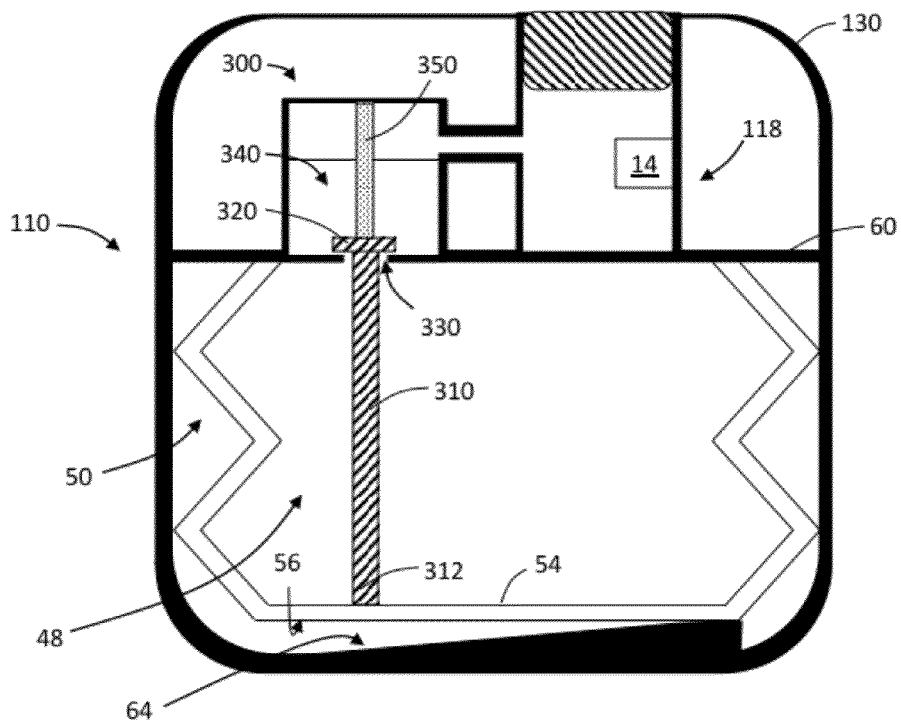
Figure 9:
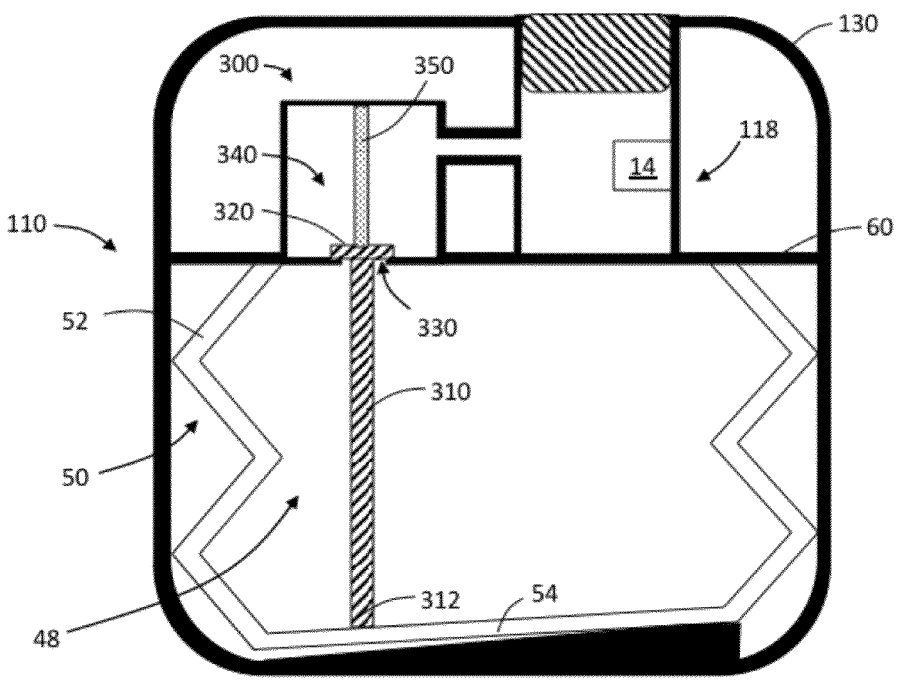

Referring now to FIGS. 8-9, an example of an infusion device 110 configuration that may be more suitable for devices 110 having bellows-type reservoirs 48 with a rigid wall that forms the surface 56 of the collapsible member 50 is shown. In this embodiment, the bottom interior surface 64 of the housing 130 is ramped such that the surface 64 engages the surface 56 of the collapsible member 50 at, or in proximity to, an edge of the surface 56 when the reservoir 48 is full. As additional fluid is introduced into the reservoir 48, the side of the bellows wall 52 opposite the edge engaging bottom interior surface 64 of the housing 130 may further expand without distorting the shape of the rigid wall that forms the surface 56 of the collapsible member 50. The OPM valve body member 310 is located and configured to contact the rigid wall that forms the surface 56 of the collapsible member 50 at a position away from the edge that contacts the elevated portion of the ramp of the bottom interior surface 64 of the housing 130 so that fluid infusion into the reservoir 48 beyond full state of the reservoir allows for additional movement of the free distal end 312 of the valve body member 310 towards a less inclined portion of the ramped surface 64. Thus, the OPM 300 valve may close (e.g., sealing of valve passageway) without distortion of the rigid bottom wall 54 of the collapsible member 50.

Figure 10:
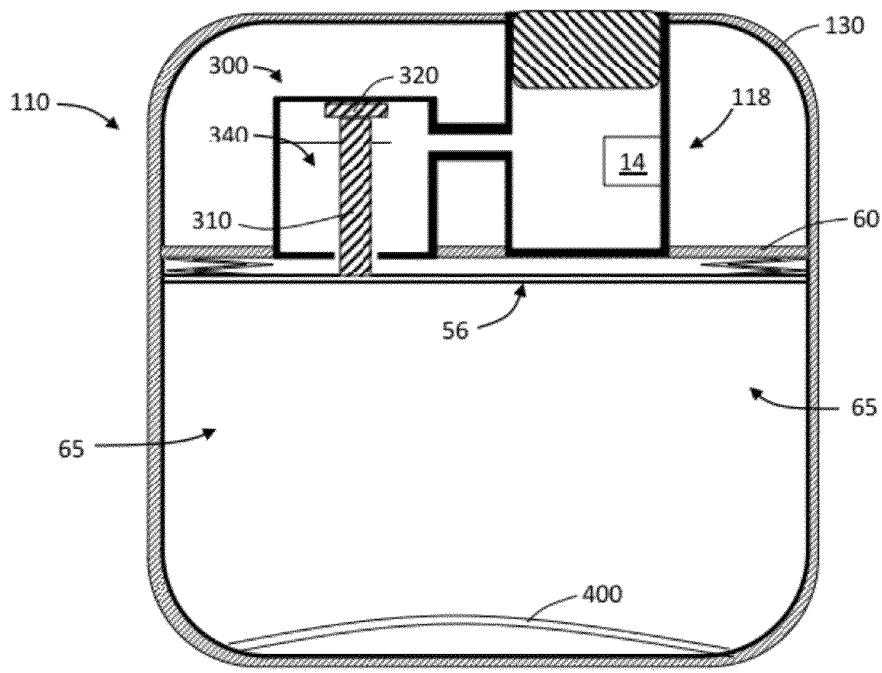
Figure 11:
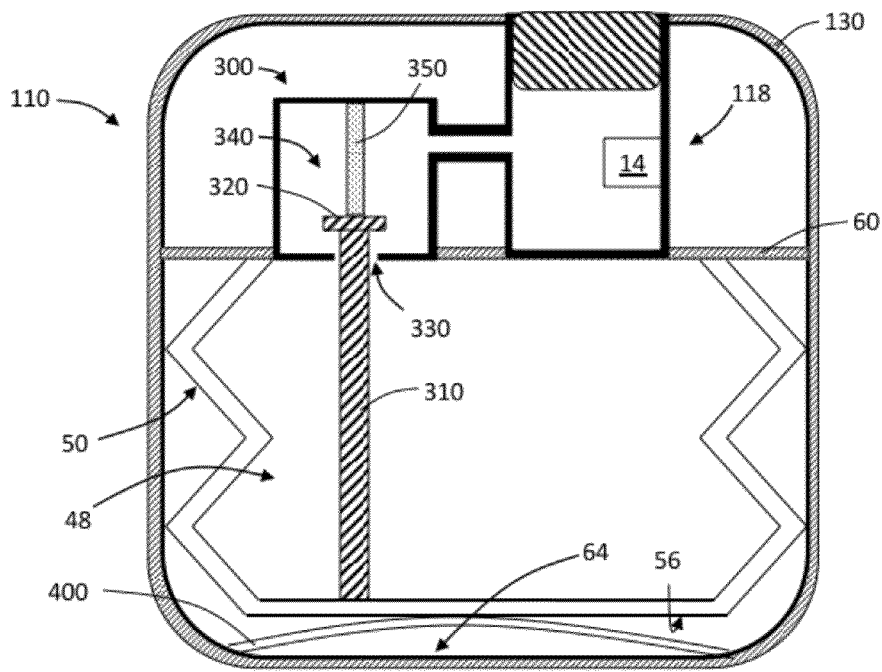
Figure 12:
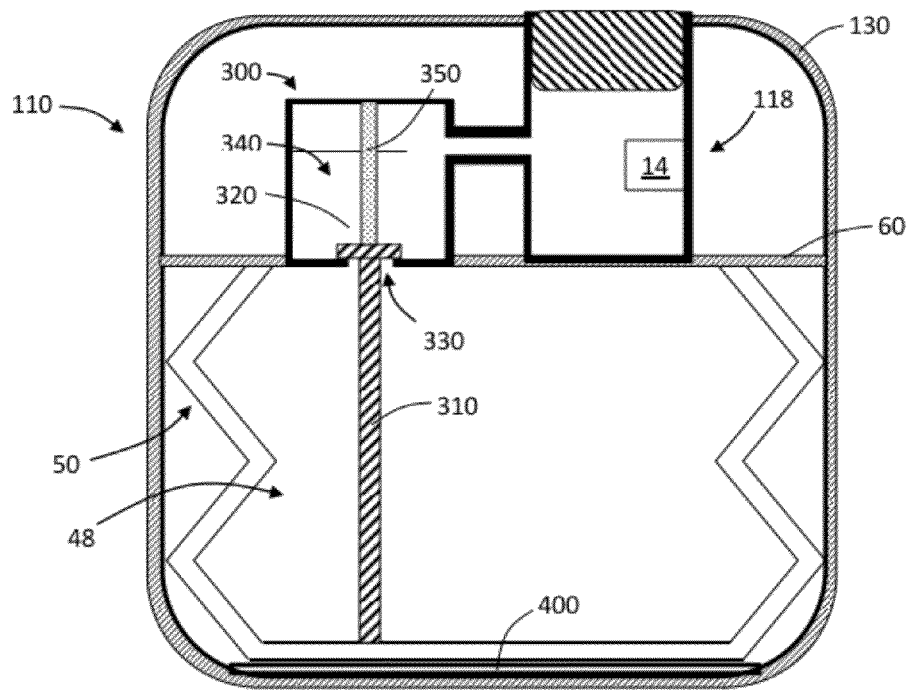

Referring now to FIGS. 10-12, an embodiment of an infusion device 110 having a deflectable or compressible member 400 as the interference member configured to engage the surface 56 of the collapsible member 50 when the reservoir is full is shown. As shown in FIG. 11, the surface 56 of the collapsible member 50 engages the deflectable member 400 when the reservoir 48 is full. At this point, the OPM 300 valve passageway 330 remains open as the valve body 310 has not fully extended. Further introduction of fluid into the reservoir 48 causes the surface 56 of the collapsible member 50 to press at least a portion of the deflectable member 400 towards the surface 64 of the housing 130, causing the OPM 300 valve passageway 330 to close (see, FIG. 12). As fluid is removed from the reservoir 48 during delivery of therapeutic agent to the patient, the deflectable member 400 returns to its original shape (see, FIGS. 10-11) and is again able to result in a detectable increase in pressure at the reservoir full position during a refill procedure as discussed above.

The implementation of a deflectable member 400, as opposed to a shaped bottom of the housing 130 as described above with regard to FIGS. 4 and 6-7, may be desirable. For example, when a deflectable member 400 is used, the deflectable member deforms and returns to its free state. Thus, the bottom surface of the collapsible member is not subjected to the same levels of deformation stresses as discussed above, providing less wear and tear on the collapsible member 50, depending on the configuration of the collapsible member. Further, pressure increases in the reservoir 48 may not be as great as would be observed when the collapsible member engages with a rigid, non-resiliently deformable interference member, such as the bottom of the housing 130. By avoiding exposure of the reservoir 48 to greatly increased pressures, the longevity of the collapsible member may be enhanced.

Any suitable resilient deflectable member 400 may be used in accordance with the teachings presented herein. Preferably, the deflectable member 400 is configured to have a spring rate suitable for causing a sufficient rise in pressure in the reservoir upon engagement of the collapsible member 50 with the deflectable member 400 and continued concomitant infusion of fluid into the reservoir 48. The deflectable member 400 may be attached to (e.g. fastened to, welded or soldered to, adhered to, or the like), or formed from, the housing 130.

In some embodiments, the deflectable member 400 is a Belleville spring attached to the housing 130. A Belleville spring can be designed to have a non-linear spring rate, with maximum stiffnesses at small deflection followed by a drop in spring rate at larger deflections—sometimes to negative spring rates. See, e.g., Design of Mechanical Elements, Chapter 8-8 Belleville Springs, pages 310-31. Such designs would result in a noticeable pressure inflection point, without an excessive increase in reservoir pressure. Use of Belleville springs or other springs, such as finger springs, that have non-linear spring rates and that would allow for a sharp step change in reservoir pressure without causing unacceptably high reservoir pressure may be used. Belleville springs can also be advantageously designed to take up very little space. For example a Belleville spring having a spring height of approximately 0.02 inches can have a height of about 0.004 inches in its fully compressed state. Thus, the addition of such a Belleville spring would add only 0.004 inches to the thickness of the infusion device.

Figure 13:
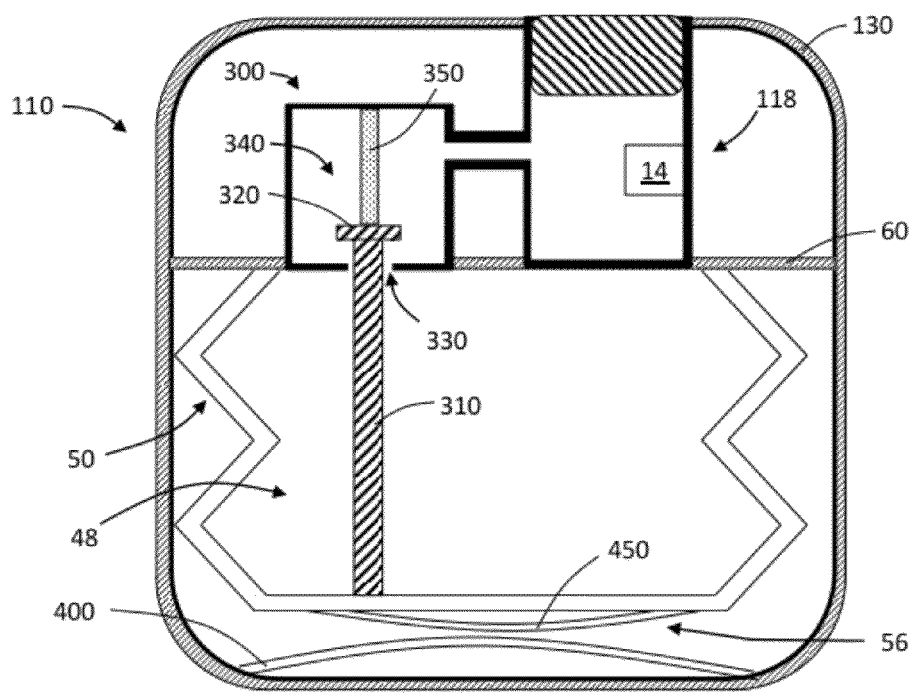

Referring now to FIG. 13, in some embodiments, two springs having non-linear spring rates, e.g. as described above, are placed in series (e.g., face-face) to amplify the desired effect of such springs. As shown in FIG. 13, one spring 450 is coupled to the bottom of the collapsible member 50 and serves as the surface 56 of the collapsible member that engages the interference member, spring 400 in this case, when the reservoir 48 is full. By placing the springs or deflectable elements 400, 450 in series, a more distinct and sharp step in reservoir pressure may be observed when the springs 400, 450 engage as the reservoir 48 is filled. If the springs 400, 450 have non-linear spring rates, where the spring rates decrease upon increased deflection, there will be an initial spike in pressure in the reservoir that will be transient, with reduced absolute pressure upon further filling (and spring deflection). This can result in a distinctive, characteristic pressure increase in the reservoir 48 that can be readily detected, but which will prevent excessive and unacceptably high reservoir pressures resulting from continued filling of the reservoir (which is in contrast to what would be observed in the embodiments depicted in FIGS. 2-9 above, particularly FIGS. 2-3).

While the springs of deflectable members are shown spanning the distance of the housing or surface of the collapsible member in FIGS. 10-13, it will be understood that the springs may expand only a portion of the distance housing or collapsible member. It will also be understood that more than one spring or deflectable member may be placed across the length, or a portion thereof, of the housing or collapsible member.

Regardless of the type of deflectable element used (or whether a deflectable element is used at all), the pressure increase, the rate of pressure increase, or a characteristic pressure profile is detectable and is preferably sufficient to distinguish from background noise or fluctuations in pressure due to changes in rate of fluid infusions, such as when infusion is stopped and suddenly started. For example, and with reference to FIGS. 14-15, simulated plots of pressure versus time (FIG. 14) and rate of change of pressure versus time ($\delta P/\delta T$, FIG. 15) at a constant rate are shown. The simulation assumes that the reservoir is being filled with fluid that is the same temperature as the infusion device. The infusion device includes a propellant and bellows reservoir having a spring constant that results in a constant rate of increase of pressure if the reservoir is filled at a constant rate with a fluid of the same temperature of as the reservoir and propellant. The arrows indicate the point at which the interference member (in this model, the interference member is rigid—e.g., surface of backshield or device housing) engages the closed end the collapsible member forming the reservoir. After initial contact, the pressure and the rate of pressure change noticeably increases with continued infusion of fluid into the reservoir. As shown in FIG. 15, the rate of change of pressure ($\delta P/\delta T$) may provide a more readily detectable and distinguishable signal than the change in pressure. However, in many cases, the change in pressure may be sufficient.

Figure 15:
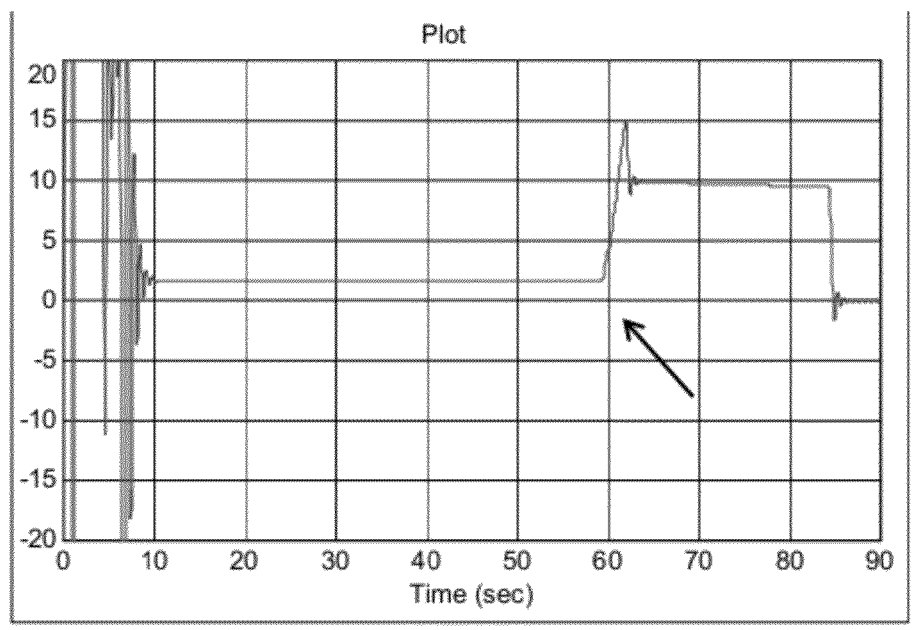
Figure 16:
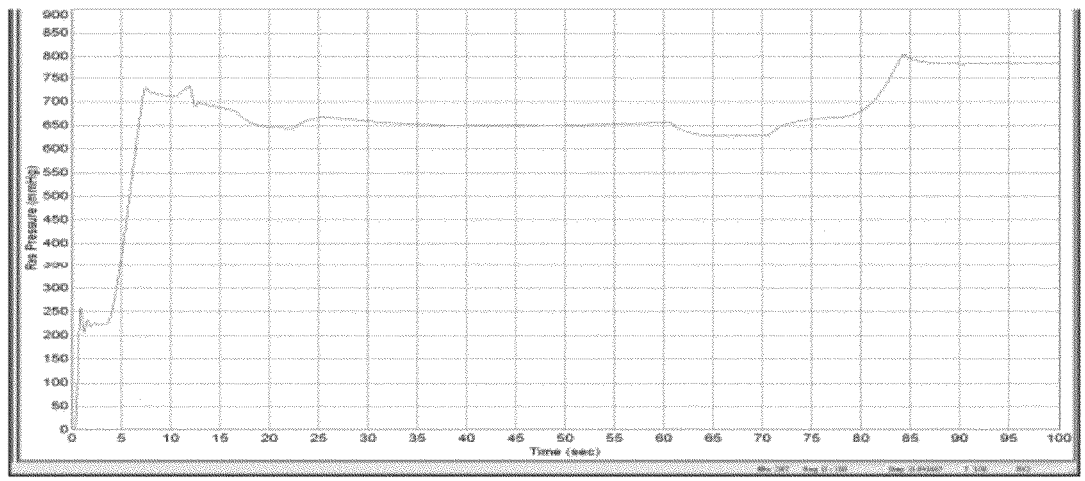
Figure 17:
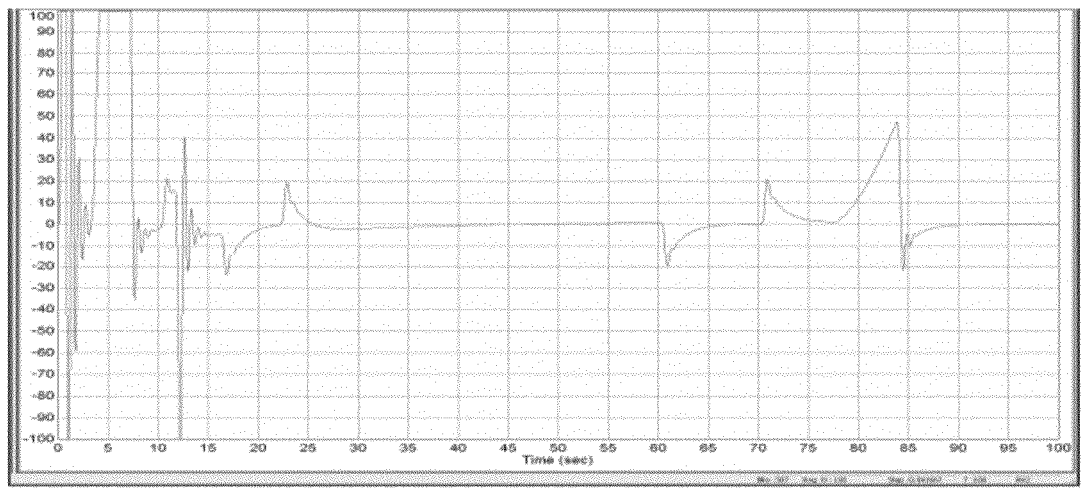

By way of further example and with reference to FIGS. 16-17, simulated plots of pressure versus time (FIG. 16) and rate of change of pressure versus time ($\delta P/\delta T$, FIG. 17) with some fluctuations in infusion rate are shown. In the depicted simulated plots, the infusion rate of fluid into the reservoir is slowed at about 16 seconds and increased at 24 seconds. In addition, the infusion rate of fluid into the reservoir is slowed just after 60 seconds, followed by an increase in infusion rate at about 70 seconds, with initial interaction with the interference member shown just prior to 80 seconds. Further, the fluid introduced into the reservoir is colder than the infusion device, as may occur with a room temperature fluid being infused into a body temperature reservoir. As with the simulated plots of FIGS. 14-15, the simulated plots of FIGS. 16-17 assume a propellant and bellows reservoir, which would have a spring constant that results will result in a constant rate of increase of pressure if the reservoir is filled at a constant rate with a fluid of the same temperature of as the reservoir and propellant. However, due to the colder temperature of the fluid filling the reservoir, the pressure response to fluid filling is different than when the fluid is the same temperature as the infusion device. The propellant is particularly sensitive to temperature fluctuations. The relatively cool temperature of the added fluid reduces the temperature of the propellant and therefore the propellant pressure, thereby causing the overall pressure of the system to stay steady, or even drop, as the colder fluid is added to the reservoir. The simulated plots shown in FIGS. 16-17 are therefore more indicative of a scenario that may be experienced in the real world than of a simulated scenario with matching fluid and device temperatures and constant infusion rate. However, as depicted in the simulated plots, the pressure changes due to interaction with an interference member can be readily distinguished from infusion rate variances that may occur during a refill procedure even with fluid of a temperature different from that of the infusion device.

Figure 14:
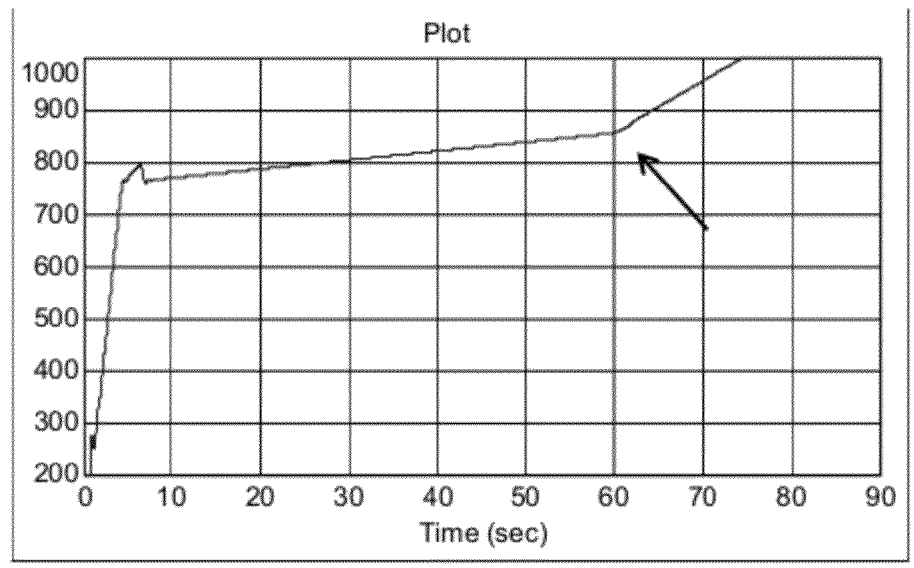
FIGS. 14-17 are simulated plots of pressure versus time or derivative of pressure versus time.

As shown in FIG. 16, which is a simulated plot of pressure versus time, pressure does not increase in a linear manner as in FIG. 14 where the fluid was the same temperature as the reservoir. As the change in pressure is subject to many variables, including relative temperature, the rate of change of pressure (FIG. 17) may allow for more reliable determinations of a pressure changes due to engagement of the reservoir with an interference member in some cases.

Of course, any suitable change in reservoir pressure may be employed in determining whether a reservoir is full (or near full) and has engaged an interference member. For example, one or more of the following may be employed: derivative of pressure ($\delta P/\delta T$) increases above a threshold value are observed; measured pressure exceeds a threshold value; pressure derivative exceeds a set threshold value for a set amount of time; measured pressure exceeds exceed a set threshold value for a set amount of time; a combination thereof; and the like.

Figure 18:
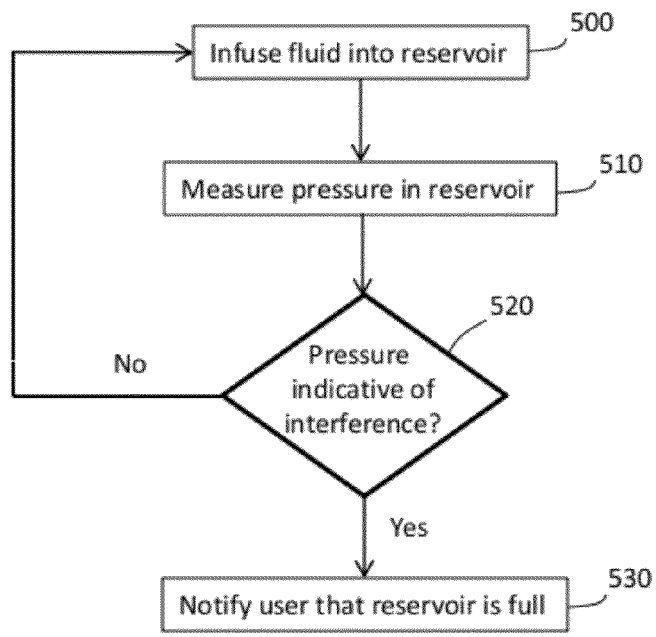
FIG. 18 is a flow diagram of an embodiment of a method.

Regardless of the algorithm employed to detect a pressure change indicative of a full reservoir in accordance with the teachings presented herein, it is desired that a user infusing fluid into the reservoir be notified that the reservoir is full. As depicted in FIG. 18, a method in accordance with the teachings presented herein includes infusing fluid into a reservoir (500), e.g. with a syringe through a refill port. The method further includes measuring pressure in the reservoir (510) and determining whether pressure is indicative of contact between a surface of the reservoir and an interference member with continued infusion (520). If the pressure is indicative of engagement with the interference member, the user may be notified that the reservoir is full (530) and may stop infusing fluid into the reservoir.

Figure 19:
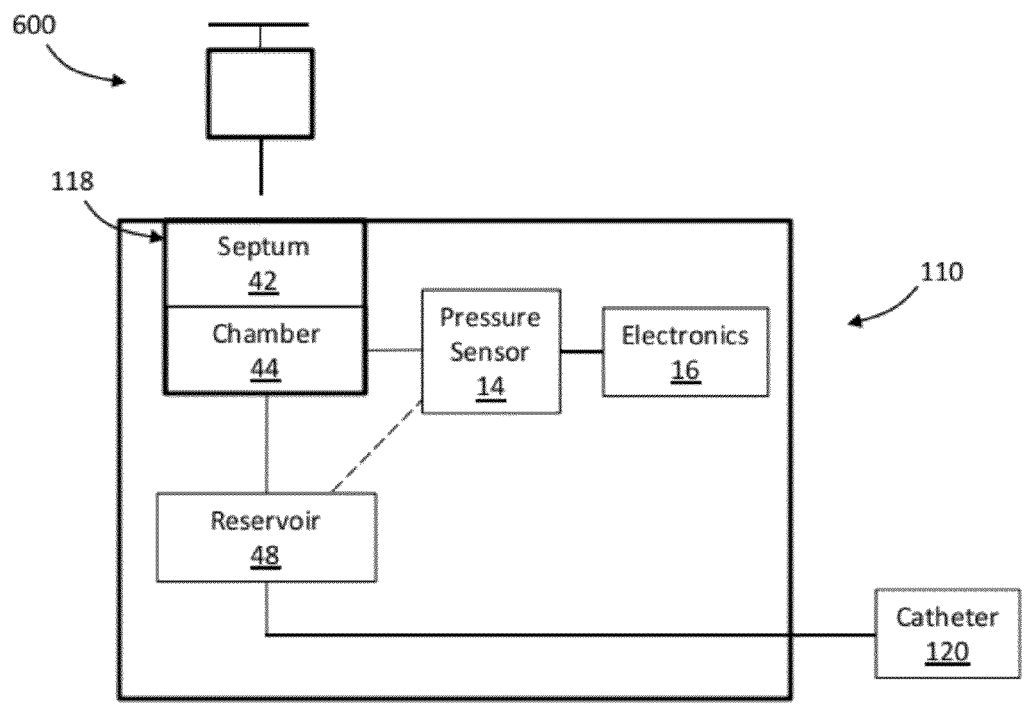
FIGS. 19-20 are schematic block diagrams showing selected components of systems in accordance with embodiments described herein.
Figure 20:
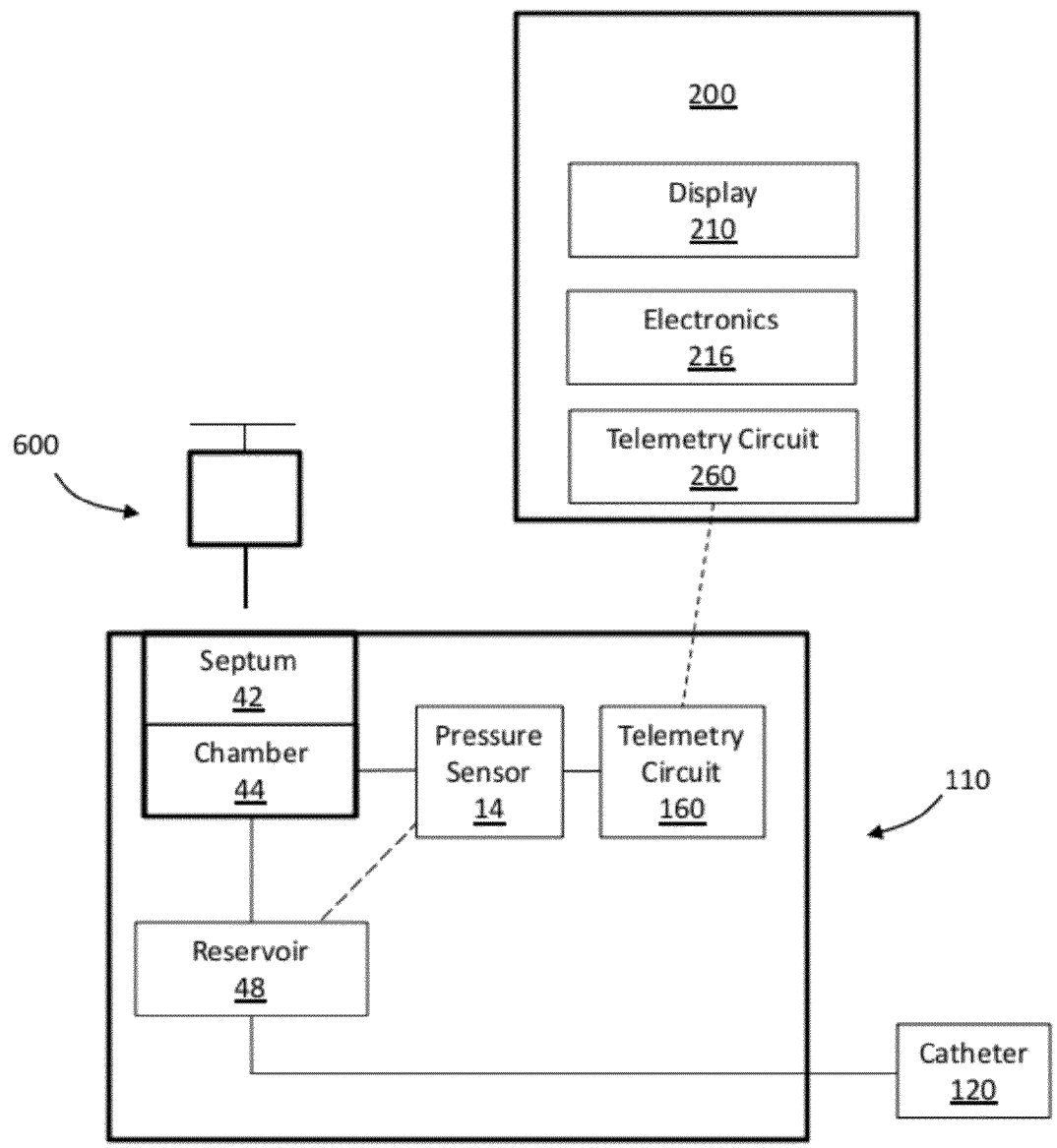

Referring now to FIGS. 19-20, schematic block diagrams showing selected components of devices and systems configured to detect a full reservoir during a filling procedure and to notify a user that the reservoir is full are depicted. FIG. 19 refers to a representative system that includes an implantable infusion device 110 and a syringe assembly 600. The syringe assembly 600 includes a needle for transcutaneously accessing an implanted infusion device 110 via a fill port 118. A self-sealing septum 42 is disposed across a chamber 44 of the fill port 118 to seal the chamber 44 from the exterior of the device 110.

The syringe assembly 600 may be preloaded with a predetermined volume of fluid, which may match the full volume of the reservoir 48. The plunger of the syringe assembly 600 may be depressed once the needle is inserted through the septum 42 and into the chamber 44 of the fill port 118. As with the embodiments described above with regard to FIGS. 2-13, the chamber 44 is in fluid communication with the reservoir 48, which may have a configuration as described above relative to an interference member for contacting a surface of the reservoir 48 when the reservoir is full. A pressure sensor 14 is in fluid communication with the reservoir 48 and may be placed any suitable place with respect to the reservoir 48, such as in chamber 44.

The pressure sensor 14 is operably coupled to electronics 16, which may include an analog to digital convertor, a band pass filter, a processor, memory, and the like. The electronics 16 (e.g. processor and memory) may be programmed with instructions for determining whether the reservoir 48 has reached full status during a fill procedure as described above. In some embodiments, the electronics 16 are configured to calculate the change in pressure over time ($\delta P/\delta T$) and may compare values of pressure and derivatives of pressure to values in lookup tables to determine whether a measure pressure or pressure profile is indicative of a surface of the reservoir engaging an interference member with concomitant additional fluid infusion into the reservoir.

In some embodiments, the electronics for determining whether the pressure in the reservoir is indicative of a full reservoir are located in an external device 200 (e.g., an external device as discussed above with regard to FIG. 1) as shown in FIG. 20. In such embodiments, the infusion device 110 includes a telemetry circuit 160 (e.g., a telemetry antenna, an analog to digital convertor, and the like) capable of communicating with a telemetry circuit 260 of the external device 200. Of course, in embodiments where implantable infusion device 110 includes the requisite electronics for making the determinations, the device 110 may also include a telemetry circuit for communicating with an external device.

In embodiments where the determinations as to whether reservoir pressure is indicative or a full reservoir 48, data transmitted from infusion device 110 to external device 200 via telemetry circuits 160/260 is processes by electronics 216 of external device, which may present the results to a user via display 210. Of course, if determinations are made by electronics of the implantable device, it may still be desirable to transmit the results to the external device for processing or display.

It will be understood that components such as a power supply, pump, and the like were omitted from the block diagrams in FIGS. 19-20 for purposes of convenience, brevity and clarity.

It will also be understood that any one or more components or steps presented with regard to embodiments described herein may be applied with regard to other embodiments. For example, the shaped interior surface 64 of the housing shown in FIG. 4 may be used in conjunction with the deflectable element 450 as shown in FIG. 13.

Thus, systems, devices and methods for DETECTING A FULL RESERVOIR OF AN IMPLANTABLE INFUSION DEVICE are described. Those skilled in the art will recognize that the preferred embodiments described herein may be altered or amended without departing from the true spirit and scope of the disclosure, as defined in the accompanying claims.

What is claimed is:

1. An implantable infusion device comprising:
   a housing;
   a collapsible member disposed within the housing and defining a reservoir for containing a variable volume of fluid and having an outer surface that moves between an empty position and a full position in response to a change in volume of fluid contained in the reservoir;
   an interference member disposed within the housing and configured to engage the outer surface of the collapsible member as the reservoir approaches the full position and to cause pressure in the reservoir to increase following engagement with the surface of the collapsible member and concomitant fluid introduction into the reservoir, wherein the collapsible member and the interference member are configured such that the reservoir is capable of further expansion after the surface of the collapsible member engages the interference member and additional fluid is added to the reservoir;
   a port in fluid communication with the reservoir for providing access to the reservoir through the housing;
   a pressure sensor in communication with the reservoir; and
   electronics operably coupled to the pressure sensor for detecting the increase in pressure associated with engagement of the interference member with the surface of the collapsible member and concomitant fluid introduction into the reservoir.

2. The device of claim 1, wherein the electronics are further configured to determine whether a sensed pressure increase is indicative of engagement of the interference member with the outer surface of the collapsible member and concomitant fluid introduction into the reservoir.

3. The device of claim 2, wherein the electronics are configured to send data to an external device via telemetry if a sensed pressure increase is indicative of engagement of the interference member with the outer surface of the collapsible member and concomitant fluid introduction into the reservoir, wherein the data is configured to relay to the external device that the reservoir is full.

4. The device of claim 1, wherein the electronics are configured to send data regarding sensed pressure to an external device via telemetry.

5. The device of claim 1, further comprising:
a bulkhead partitioning the housing to form a chamber having an interior surface,
wherein the collapsible member is disposed within the chamber, wherein movement of the outer surface of the collapsible member from the reservoir empty position to the reservoir full position causes the surface of the collapsible member to approach the interior surface of the chamber.

6. The device of claim 5, wherein the collapsible member forms a bellows reservoir having a cylindrical wall sealingly attached to the bulkhead.

7. The device of claim 5, wherein the interference member is the interior surface of the chamber.

8. The device of claim 7, wherein the interior surface of the chamber is shaped to contact a first portion of the surface of the collapsible member when the reservoir is full and to contact a second portion of the surface of the collapsible member when additional fluid is added to the reservoir, wherein the surface area of the second portion is greater than the surface area of the first portion.

9. The device of claim 5, wherein the interference member is disposed between the surface of the collapsible member and the interior surface of the chamber.

10. The device of claim 5, wherein the interference member is coupled to the interior surface of the chamber.

11. The device of claim 5, wherein the interference member comprises a resiliently deflectable element.

12. The device of claim 5, wherein the interference member comprises a Belleville spring.

13. The device of claim 1, further comprising an overpressurization mechanism (OPM) configured to prevent flow of fluid into the reservoir via the port when the volume of the reservoir exceeds the reservoir volume at which the surface of the collapsible member initially engages the interference member.

14. The device of claim 13, wherein the OPM comprises:
an OPM chamber disposed between the port and the reservoir,
a valve passageway fluidly coupling the OPM chamber to the reservoir,
a valve assembly comprising a telescoping valve body slidably moveable through the valve passageway, the valve body portion having a distal end configured to abut an interior surface of the collapsible member that generally opposes the outer surface of the collapsible member that is configured to engage the interference member,
wherein the valve assembly is configured to sealingly engage the valve passageway when the distal end of the valve body extends a predetermined distance beyond the valve passageway,
wherein the predetermined distance is greater than the distance from the valve passageway to the interior surface of the collapsible member when the outer surface of the collapsible member initially contacts the interference member when the reservoir is being filled.

15. The device of claim 14, wherein the interference member comprises a resiliently deflectable element.

16. The device of claim 14, wherein the interference member comprises a Belleville spring.

17. The device of claim 1, wherein the interference member comprises a resiliently deflectable element.

18. The device of claim 1, wherein the interference member comprises a Belleville spring.

19. The device of claim 1, wherein the interference member is shaped to contact a first portion of the surface of the collapsible member when the reservoir is full and to contact a second portion of the surface of the collapsible member when additional fluid is added to the reservoir, wherein the surface area of the second portion is greater than the surface area of the first portion.

20. A system comprising:
an implantable infusion device according to claim 1, wherein the electronics are configured to
determine whether a sensed pressure increase is indicative of engagement of the interference member with the outer surface of the collapsible member and concomitant fluid introduction into the reservoir, and
send data to an external device if a sensed pressure increase is indicative of engagement of the interference member with the outer surface of the collapsible member and concomitant fluid introduction into the reservoir, wherein the data is configured to relay to the external device that the reservoir is full; and
an external device configured to receive the data from the implantable infusion device and to display that the reservoir is full.

21. A system comprising:
an external device configured to receive data regarding sensed pressure from a device according to claim 1, to determine whether the sensed data is indicative of engagement of the interference member with the outer surface of the collapsible member and concomitant fluid introduction into the reservoir, and to display that the reservoir is full if the sensed data is indicative of engagement of the interference member with the outer surface of the collapsible member and concomitant fluid introduction into the reservoir; and
a device according to claim 1, wherein the electronics are configured to send data regarding the sensed pressure to the external device.

* * * * *